United States Patent [19]
Veerapaneni et al.

[11] Patent Number: 6,087,172
[45] Date of Patent: Jul. 11, 2000

[54] RIBOZYMES TARGETED TO HUMAN IL-15 MRNA

[75] Inventors: Dange Veerapaneni, San Diego, Calif.; Shoji Hamanaka, Kanagawa; Iwao Nozawa, Tokyo, both of Japan

[73] Assignee: Hisamitsu Pharmaceutical Co., Inc., Saga, Japan

[21] Appl. No.: 08/962,503

[22] Filed: Oct. 31, 1997

[51] Int. Cl.[7] .............................. C07H 21/04; C12Q 1/68; C12N 15/00

[52] U.S. Cl. ......................... 435/375; 435/6; 435/91.31; 435/320.1; 435/325; 435/366; 435/455; 536/23.1; 536/23.2; 536/24.31; 536/24.33; 536/24.5

[58] Field of Search .......................... 435/6, 91.31, 440, 435/375, 325, 366, 455; 536/23.1, 23.2, 24.5, 24.3; 514/44; 800/13, 18

[56] References Cited

U.S. PATENT DOCUMENTS

| | | | |
|---|---|---|---|
| 4,987,071 | 1/1991 | Cech et al. | 435/91 |
| 5,496,698 | 3/1996 | Draper et al. | 435/6 |
| 5,525,468 | 6/1996 | McSwiggen | 435/6 |
| 5,616,490 | 4/1997 | Sullivan et al. | 435/366 |
| 5,626,488 | 5/1997 | Sullivan et al. | 435/366 |
| 5,660,824 | 8/1997 | Grabstein et al. | 424/85.2 |

FOREIGN PATENT DOCUMENTS

| | | |
|---|---|---|
| WO 95/10607 | 4/1995 | WIPO . |
| 9527722 | 10/1995 | WIPO . |
| WO 98/18812 | 5/1998 | WIPO . |

OTHER PUBLICATIONS

Canals et al. J. Inerteron & Cytokine Res. 17:473–480 (1997).
Canals et al. Gene 195: 337–339.
Meazza et al. Oneogene 12: 2187–2192, 1996.
Meazza et al. Eur. J. Immunol. 27:1049–1054, 1977.
Branch TIBS 23:45–50, Feb. 1998.
Gir: et al. EMBO J. 14:3654–3663, 1995.
Anderson et al. Genomics 25: 701–706, 1995.
Reinecker et al. Gastroenterology 111:1706–1713, 1996.
Rossi et al. Aids Reseach & Human Retroviruses 8:183, 1992.
Hempel et al. Biochemistry 28:4929, 1989.
Perrotta et al. Biochemistry 31:16, 1992.
Guerrier–Takada et al. Cell 35:849, 1983.
Saville et al. Cell 61:685, 1990.
Flanagan et al. Nature Biotechnology 17:48–52, 1999.
Crooke, S.T. Ch1 from "Antisense Research & Application", Springer, 1998.
Minghetti et al., Abstract: TNF–a Ribozymes and Antisense Molecules as Potential Therapeutic Agents for Treatent of Rheumatoid Arthritis.
Taylor et al., "Chimeric DNA–RNA hammerhead ribozymes have enhanced in vitro catalytic and increased stability in vivo" Nucleic Acid Research, vol. 20, No. 17, pp. 4559–4565 (1992).

McInnes et al., "Interleukin–15 mediates T cell–department regulation of tumor necrosis factor–α production in rheumatoid arthritis", Nature Medicine, vol. 3, No. 2, (Feb. 1997).

Grabstein et al., "Cloning of a T cell growth factor that interacts with the beta chain of the interleukin–2 receptor", Science, 264, 965–968 (1994) GenBank.

Uhlenbeck, "A small catalytic oligoribonucleotide", Nature, vol. 328, Aug. 19, 1987 pp. 596–600.

McInnes et al., "The role of interleukin–15 in T–cell migration and activation in rheumatoid arthritis", Nature, vol. 2, No. 2, Feb. 1996, pp. 175–182.

McInnes et al., Interleukin–15 mediates T cell–dependent regulation of tumor necrosis factor–α production in rheumatoid arthritis, Nature, vol. 3, No. 2, Feb., 1997, pp. 189–195.

Blauvelt et al., "Interleukin–15 mRNA Is Expressed by Human Keratinocytes, Langerhans Cells, and Blood–Derived Dendritic Cells and Is Downregulated by Ultraviolet B Radiation", The Journal of Investigative Dermatology, vol. 106, No. 5, May 1996, pp. 1047–1052.

Taylor et al., "Chimeric DNA–RNA hammerhead ribozymes have enhanced in vitro catalytic efficiency and increased stability in vivo," Nucleic Acids Research, vol. 20, No. 17 pp. 4559–4565.

Fell et al., "Cellular Uptake Properties of a 2'–Amino/2'–O–Methyl–Modified Chimeric Hammerhead Ribozyme Targeted to the Epidermal Growth Factor Receptor mRNA", Antisense & Nucleic Acid Drug Development, 7:319–326 (1997), pp. 319–326.

Ghivizzani et al., "Direct retrovirus–mediated gene transfer to the synovium of the rabbit knee: implications for arthritis gene therapy", Gene Therapy 1997 4:977–982.

*Primary Examiner*—John L. LeGuyader
*Attorney, Agent, or Firm*—Fish & Richardson, P.C.

[57] ABSTRACT

Enzymatic RNA molecules which cleave mRNA encoding IL-15, are provided. The constructs of the invention include regulatory regions for expression in cells, cell lines, or transgenic non-human animals. The ribozymes of the invention are directed against IL-15 mRNA and are useful in treating rheumatoid arthritis.

20 Claims, 6 Drawing Sheets

```
   1 tgtccggcgc cccccgggag ggaactgggt ggccgcaccc tcccggctgc ggtggctgtc
  61 gcccccacc ctgcagccag gactcgatgg agaatccatt ccaatatatg gccatgtggc
 121 tctttggagc aatgttccat catgttccat gctgctgctg acgtcacatg gagcacagaa
 181 atcaatgtta gcagatagcc agcccataca agatcgtatt gtattgtagg aggcatcgtg
 241 gatggatggc tgctggaaac cccttgccat agccagctct tcttcaatac ttaaggattt
 301 accgtggctt tgagtaatga gaatttcgaa accacatttg agaagtattt ccatccagtg
 361 ctacttgtgt ttactttctaa acagtcattt tctaactgaa gctggcattc atgtcttcat
 421 tttgggctgt ttcagtgcag ggcttcctaa aacagaagcc aactgggtga atgtaataag
 481 tgatttgaaa aaaattgaag atcttattca atctatgcat attgatgcta ctttatatac
 541 ggaaagtgat gttcacccca gttgcaaagt aacagcaatg aagtgctttc tcttggagtt
 601 acaagttatt tcacttgagt ccggagatgc aagtattcat gatacagtag aaaatctgat
 661 catcctagca aacaaacagt tgtcttctaa tgggaatgta acagaatctg gatgcaaaga
 721 atgtgaggaa ctggaggaaa aaaatattaa agaattttttg cagagttttg tacatattgt
 781 ccaaatgttc atcaacactt cttgattgca attgattctt tttaaagtgt ttctgttatt
 841 aacaaacatc actctgctgc ttagacataa caaaacactc ggcatttaaa atgtgctgtc
 901 aaaacaagtt tttctgtcaa gaagatgatc agacccttgga tcttagaaat
 961 gaaggcagaa aaatgtcatt gagtaatata gtgactatga acttctctca gacttacttt
1021 actcatttt ttaatttatt attgaaattg tacatatttg tggaataatg taaaatgttg
1081 aataaaaata tgtacaagtg ttgttttta agttgcactg atatttacc tcttattgca
1141 aaatagcatt tgtttaaggg tgatagtcaa attatgtatt ggtggggctg ggtaccaatg
1201 ct
SEQ ID NO:11
```

FIG. 8

IL-15 DNA/RNA Ribozymes:

HK-RT-97: 5' UUC UAA ACA GUC AUU UUC UAA 3'   SEQ ID NO:2

HK-RZ-97: 5' TTA GAA AAT cug aug agT CCG TGA GGA cga aaC tgt TTAGAA 3'   SEQ ID NO:1

HK-RT-126: 5' GGC AUU CAU GUC UUC AUU UUG 3'   SEQ ID NO:4

HK-RZ-126: 5' CAA AAT GAA cug aug agT CCG TGA GGA cga aaC ATG AAT GCC 3'   SEQ ID NO:3

HK-RT-331: 5' UUC ACA UGA GUC CGG AGA TAC 3'   SEQ ID NO:6

HK-RZ-331: 5' GTA TCT CCG cug aug agT CCG TGA GGA cga aaC TCA TGT GAA 3'   SEQ ID NO:5

HK-RT-394: 5' AAC AUC UUG UCU UCU AAU GG 3'   SEQ ID NO:8

HK-RZ-394: 5' CC ATT AGA Acu gau gag TCC GTG AGG Acg aaa CAA GAT GTT 3'   SEQ ID NO:7

HK-RT-491: 5' GUA CAU AUU GUC CAA AUG UUC 3'   SEQ ID NO:10

HK-RZ-491: 5' GAA CAT TTG cug aug agT CCG TGA GGA cga aaC AAT ATG TAC 3'   SEQ ID NO:9

FIG. 9

RIBOZYMES TARGETED TO HUMAN IL-15 MRNA

FIELD OF THE INVENTION

This invention relates generally to the field of therapeutic compositions and more specifically to methods of treatment for diseases associated with interleukin-15 (IL-15), such as rheumatoid arthritis.

BACKGROUND OF THE INVENTION

There are a number of diseases known in humans that affect the joints, and particularly the synovium. These include synovial sarcomas, osteoarthritis, bacterial and fungal infections, and inflammatory, autoimmune, and hemorrhagic diseases. Combined, they are a cause of great pain and suffering in the population, with little effective therapy apart from symptomatic treatment with analgesics and anti-inflammatory drugs (reviewed by Gardner, 1994 *J. Anat.* 184:465–76).

Rheumatoid arthritis (RA) affects one percent of the population worldwide. There is significant immunological activity within the synovium during the course of the disease. It is believed that this reactivity provides an intense stimulus to the synovial lining cells, which then undergo a transformation into an invasive pannus that brings about joint erosion through the release of destructive mediators. The release of cytokines, proteases, and reactive oxygen intermediates, have all been implicated in the disease pathology. The initiating factor is unknown, but might be an infection, trauma, bacterial infection, or autoreactivity. For example, there is increased risk of developing rheumatoid arthritis for persons having the HLA-Dw4 allele.

Chronic rheumatoid arthritis is characterized by infiltration of the normally relatively acellular synovial membrane by macrophages, T cells, and plasma cells, and with the presence of activated fibroblast-like synoviocytes (Duke, O., et al, 1982, *Clin. Exp. Immunol.* 49:22–30). There are several reports in the literature which document the presence the cytokines of macrophage derivation including IL-1, IL-1β, IL-6, IL-8, IL-15, GM-CSF, and TNF-α in synovial proliferation. Cytokines associated with T cell activation such as IFN-γ, and IL-2 have also been detected in rheumatoid arthritis. The role of various cytokines and proteases in rheumatoid arthritis is discussed in Feldmann et al., 1994 *Circ. Shock* 43:179–84; and Testa et al, 1994 *Clin. Orthop.* 308:79–84. Therapies directed at T cells, such as cyclosporin A and monoclonal antibodies against T-cell surface antigens, can produce significant clinical improvement. However, additional therapies for rheumatoid arthritis are still needed.

SUMMARY OF THE INVENTION

This invention relates to ribozymes, or enzymatic RNA molecules, that bind to and cleave mRNA encoding IL-15. The selection and function of ribozymes capable of cleaving IL-15 mRNA, and their use to reduce activity of IL-15 in tissues to treat diseases such as rheumatoid arthritis is described. The invention features use of ribozymes to treat rheumatoid arthritis by inhibiting the synthesis of IL-15 in lymphocytes and preventing the recruitment and activation of macrophages.

The invention features isolated enzymatic RNA molecules which specifically cleave mRNA encoding interleukin-15 (IL-15). The invention also features transgenic mice carrying transgenes which specifically cleave mRNA encoding IL-15.

In another embodiment, the invention features a method for suppressing IL-15 production in a cell by administering to the cell an amount of an enzymatic RNA molecule sufficient to specifically cleave mRNA encoding interleukin-15 (IL-15), thereby suppressing IL-15 levels.

In another aspect the invention features a method for treating a patient having or at risk of having a disorder associated with IL-15, by administering to the patient an effective amount of an enzymatic RNA molecule which specifically cleaves mRNA encoding interleukin-15. The IL-15 disorder may be an inflammatory disorder, for example. In a particular embodiment, the disorder is rheumatoid arthritis.

In still another aspect, the invention provides a pharmaceutical composition for treatment of a disorder associated with IL-15.

The invention provides several advantages. For example, the ribozymes or the invention are highly specific for IL-15 mRNA. Another advantage of the present invention is the ability of the ribozyme to act enzymatically. Thus, a single ribozyme molecule is able to cleave many molecules of target mRNA, and the concentration of ribozyme necessary to effect a therapeutic treatment is lower than that of an antisense oligonucleotide. A further advantage of the present invention is that the enzymatic nucleic acid molecules can be delivered exogenously or can be expressed from DNA or RNA vectors that are delivered to specific cells.

Other features and advantages of the invention will be apparent from the following detailed description, and from the claims.

DETAILED DESCRIPTION OF THE INVENTION

The ribozymes of the present invention effectively reduce IL-15 expression and can be used to treat disease induced by IL-15, such as rheumatoid arthritis (RA). The ribozymes can be delivered to cells in culture or to cells or tissues in humans or animal models of arthritis. The ribozyme-induced cleavage of IL-15 can be used to prevent inflammatory cell function and to alleviate disease symptoms.

It has been shown that IL-15 is present in RA synovium, and that IL-15 can induce TNF-α production in RA through the activation of synovial T cells (McInnes et al., 1996, *Nature Medicine*, 2:175–82). Moreover, it was shown that peripheral blood (PB) T cells activated by IL-15 induced significant TNF-0: production by macrophages via a cell contact dependent mechanism (McInnes et al., 1997, *Nature Medicine* 3:189–195). IL-15 has also been shown to be a chemoattractant for T cells in vitro, and can induce proliferation of peripheral blood and synovial cells (McInnes et al., op. cit.), and may play a role in activating antigen specific Th, cells. The present invention provides useful ribozymes directed against mRNA encoding IL-15 to reduce levels of IL-15 protein, thereby affecting the immunologic and chemoattractant functions of T cells.

An "enzymatic RNA molecule" also called a "ribozyme," or a "catalytic RNA molecule," is an RNA, DNA, or a chimeric RNA/DNA molecule, which has a nucleotide sequence that is complementary to a specified mRNA target, and also has an enzymatic activity which specifically cleaves the target mRNA. Preferably, the ribozyme is chimeric, so that in the catalytic portion or the ribozyme, the catalytic center of each of the ribozymes contains ribonucleotides, whereas the stems contain deoxyribonucleotides. The DNA/RNA composition offers improved stability in vivo and enhanced cellular activity (Taylor et al., 1992, *Nucleic Acids Res.* 20: 455–65, herein incorporated by reference.) However, the ribozymes of the invention can be also composed solely of either DNA or RNA. Preferably the target sequence is at least about 5 bases complementary to the target gene, e.g., interleukin 15 (IL-15), mRNA.

The enzymatic RNA molecules of the invention are able to inter-molecularly cleave and thereby inactivate the target mRNA molecule. The complementary sequence allows sufficient hybridization of the enzymatic RNA molecule to the target mRNA to allow the cleavage to occur. One hundred percent complementarity is preferred, but complementarity as low as 50–75% can also be useful in this invention. The ribozymes are engineered to be sequence-specific so that only mRNAs with sequences complementary to the construct containing the ribozyme are targeted and thus inactivated. The enzymatic RNA molecules of the invention consist of two regions, an "enzymatic portion" which can catalyze the hydrolysis of RNA phosphodiester bonds in trans (and thus can cleave target RNA molecules) under physiological conditions, and a "target binding portion" which specifically binds to the IL-15 target mRNA, and which is held in close proximity to the enzymatic portion. Together these regions of the molecule act to specifically cleave the target RNA.

A "stem loop" structure is a nucleic acid structure that includes one or more folding pattern which form hairpins and flank the antisense targeting sequence. The stem loop structures are preferably unmodified, naturally occurring structures. Alternatively the structures can be synthesized to mimic the naturally occurring structures.

As used herein, the term "nucleic acid" or nucleic acid sequence" refers to a polymer of deoxyribonucleotides or ribonucleotides, in the form of a separate fragment or as a component of a larger construct. For example, nucleic acids can be assembled from cDNA fragments or from oligonucleotides to generate a synthetic gene which is capable of being expressed in a recombinant transcriptional unit. Polynucleotide or nucleic acid sequences of the invention include DNA, RNA, and cDNA sequences.

A "promoter" is a minimal DNA sequence sufficient to direct transcription of a DNA sequence to which it is operably linked. A "promoter" also includes promoter elements sufficient for promoter-dependent gene expression controllable for cell-type specific expression, tissue-specific expression, or inducible by external signals or agents; such elements may be located in the 5' or 3' regions of the native gene.

The term "operably associated" refers to functional linkage between the regulatory (e.g. promoter) sequence and the nucleic acid regulated by the regulatory sequence. The operably linked regulatory sequence controls the expression of the product. The regulatory sequence may be heterologous to the desired gene sequence.

A "vector" is any compound or formulation, biological or chemical, that facilitates transformation or transfection of a target cell with a DNA of interest. Exemplary biological vectors include viruses, particularly attenuated and/or replication-deficient viruses. Exemplary chemical vectors include lipid complexes and DNA constructs.

To "inhibit" or "inhibiting" activity is to reduce that activity a measurable amount, preferably a reduction of at least 30% or more. Where there are multiple different activities that may be inhibited (for example, ribozymes that cleave mRNA encoding IL-15 may have the ability to reduce the recruitment of macrophages, and may also have the ability to decrease T cell proliferation), the reduction of any single activity (with or without the other activities) is sufficient to fall within the scope of this definition.

To "specifically cleave" is to preferably degrade a particular RNA species. The specificity of the cleavage can be determined by standard molecular assays, such as RNAse protection.

A "suppressive-effective" amount is that amount of the construct, and thus antisense, administered is sufficient to suppress the expression of the target, e.g., inhibit translation of mRNA, by at least 75% of the normal expression, and preferably by at least 90%. The effectiveness of the construct can be determined phenotypically or by standard Northern blot analysis or immunohistochemically, for example. Other standard nucleic acid detection techniques or alternatively immunodiagnostic techniques will be known to those of skill in the art (e.g., Western or Northwestern blot analysis).

A "transgenic animal" is an animal that includes a transgene that is inserted into an embryonal cell and becomes a part of the genome of the animal which develops from that cell, or an offspring of such an animal. In the transgenic animals described herein, the transgene causes specific tissue cells to express a ribozyme which specifically cleaves IL-15 mRNA. Any animal that can be produced by transgenic technology is included in the invention, although mammals are preferred. Preferred mammals include non-human primates, sheep, goats, horses, cattle, pigs, rabbits, and rodents such as guinea pigs, hamsters, rats, gerbils, and mice.

A "transgene" is a DNA sequence that includes one or more selected DNAs, e.g., encoding ribozymes that cleave mRNA encoding IL-15, to be expressed in a transgenic animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected DNA, all operably linked to the selected DNA, and may include an enhancer sequence.

An "disorder associated with IL-15" is any disease state associated with the expression of IL-15. An example of such a disorder is rheumatoid arthritis. Ribozymes Six basic varieties of naturally-occurring enzymatic RNAs are known: hammerhead ribozymes, hairpin ribozymes, Hepatitis Delta Virus Ribozymes, Tetrahymena (Group I Introns) ribozymes, RNaseP RNA (Ml RNA), and Neurospora VS RNA Ribozymes (see U.S. Pat. No. 5,616,488, herein incorporated by reference). Each can catalyze the hydrolysis of RNA phosphodiester bonds in trans (and thus can cleave target RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target mRNA. Strategic cleavage of such a target RNA will destroy its ability to direct synthesis of an encoded protein. After an enzymatic nucleic acid has bound and cleaved the RNA target, it is release from the target RNA, and can thus repeatedly bind and cleave targets.

The enzymatic nucleic acid molecule can be a hammerhead or hairpin motif ribozyme, but the ribozyme may also be formed in the motif of a hepatitis delta virus, group I intron or RNASE P RNA, or Neurospora VA RNA (for examples of the motifs see Rossi et al., 1992, *AIDS Research and Human Retroviruses* 8:183; Hampel and Triz, 1989, *Biochemistry* 28: 4929; Perrotta and Been, 1992, *Biochemistry* 31:16; Guerrier-Takada et al., 1983, *Cell* 35:849; Saville and Collins, 1990, *Cell* 61:685; Cech et al., U.S. Pat. No. 4,987,071).

The ribozymes of the invention have a specific substrate binding portion which is complementary to a target gene region of IL-15 mRNA, and have nucleotide sequences within or surrounding the substrate binding site which impart an RNA cleavage activity to the molecule. The binding portion of the new ribozymes can be used in combination with any of the enzymatic motifs. Two illustrated target binding sequences, described herein as SEQ ID NO:2 and SEQ ID NO:4, and two specific enzymatic RNA molecule nucleic acid constructs are provided, described herein as SEQ ID NO:1 and SEQ ID NO:3. These two constructs have been shown to specifically cleave IL-15 mRNA.

Figure 8:
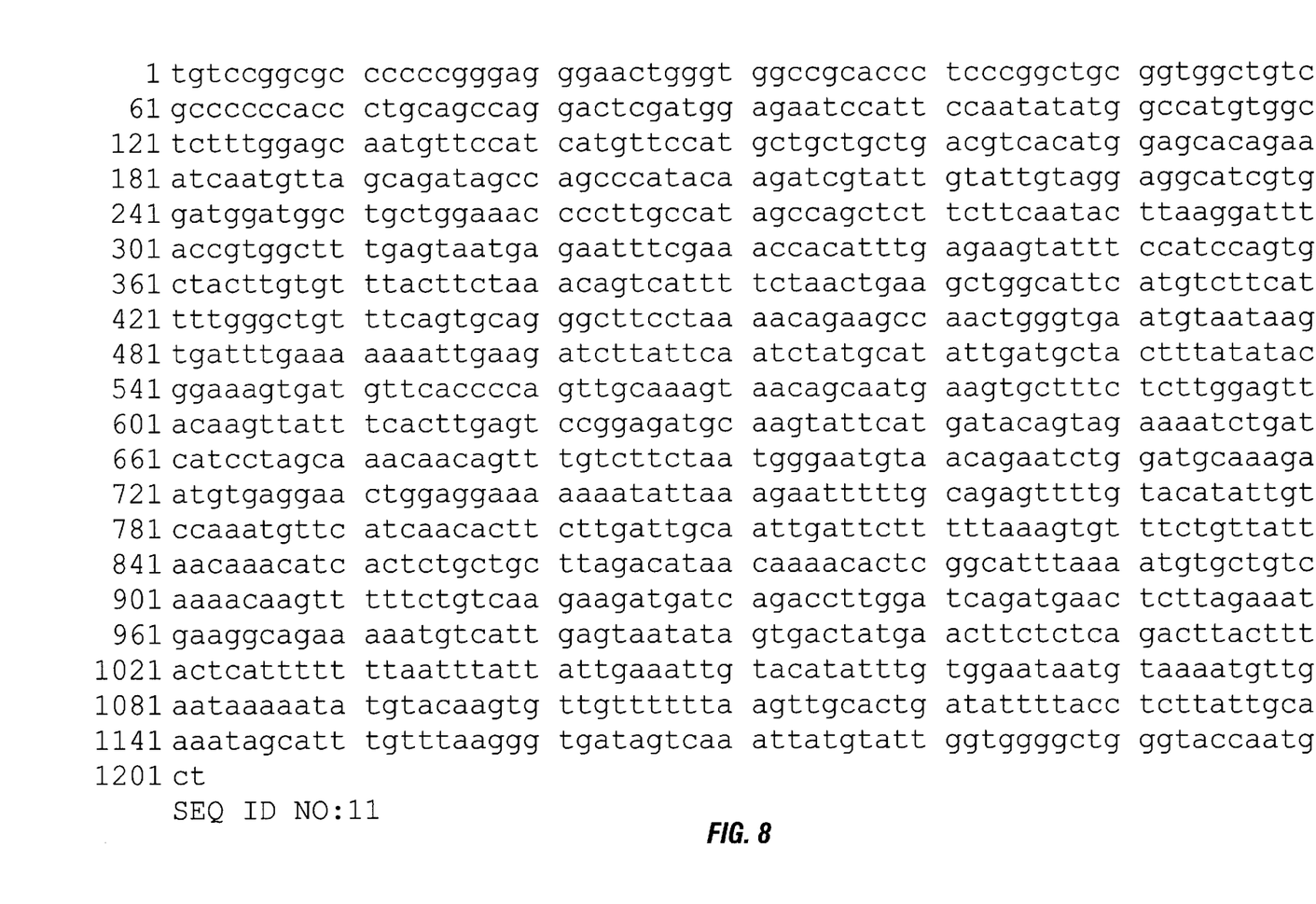
FIG. 8 is a diagram of human IL-15 mRNA (SEQ ID NO:5) (GenBank U14407). The underlining indicates the regions of the gene targeted by the ribozymes of the invention.
Figure 9:
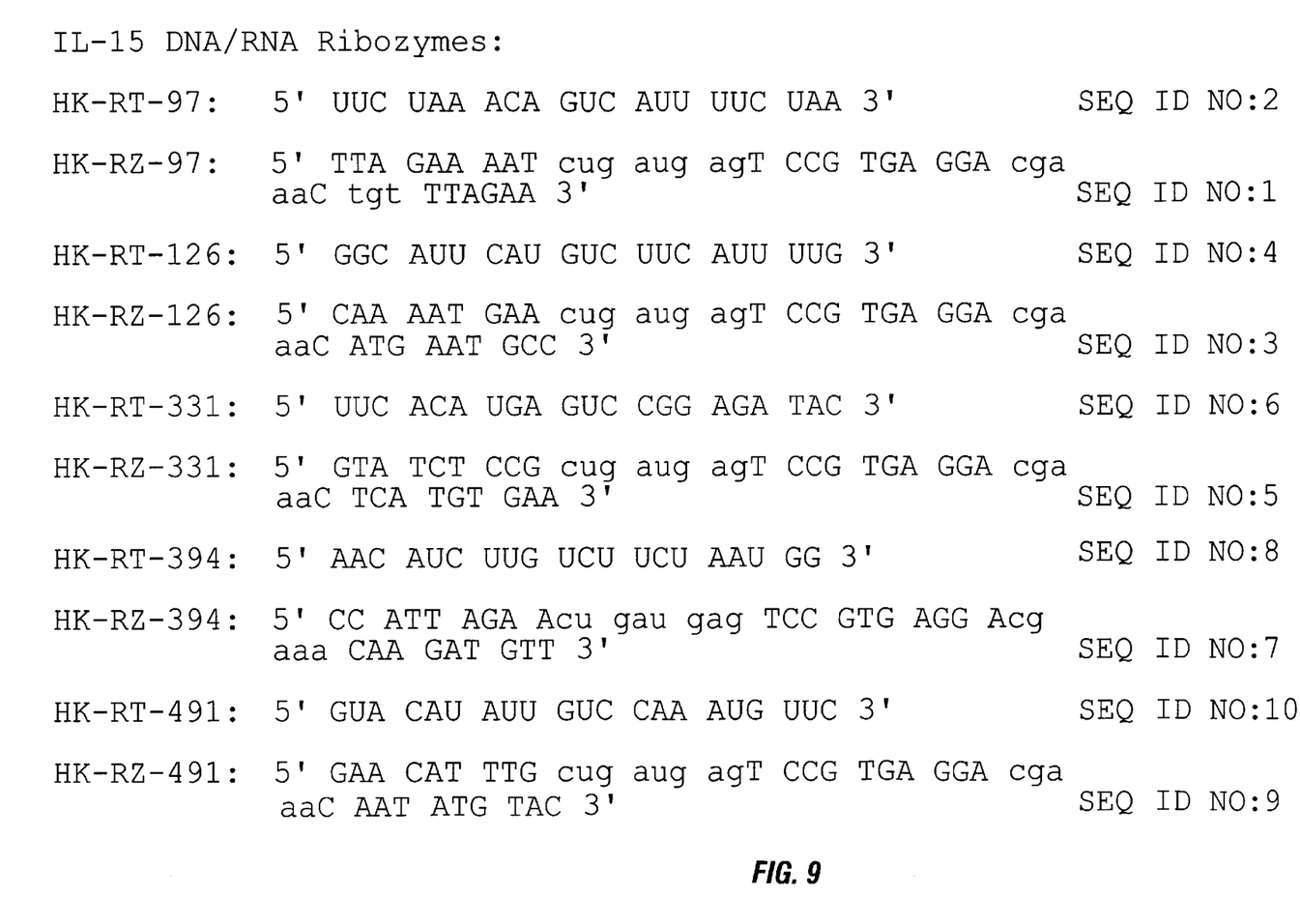
FIG. 9 shows the nucleotide sequences of the ribozymes of the invention. The target sequences (RT) and the complete ribozyme sequences (RZ) are shown (SEQ ID NO:1–10).

The sequence 5'-GUC-3' (RNA) is the cleavage site for hammerhead ribozymes (Uhlenbeck, *Nature* 328:596–600, 1987, incorporated herein by reference). The enzymatic mRNA of the invention can be targeted for binding to the GTC sequences contained in the IL-15 sequence, for example, at positions 59–77 (SEQ ID NO:2); positions 88–110 (SEQ ID NO:4); positions 293–314 (SEQ ID NO:6); positions 358–378 (SEQ ID NO:8); and positions 455–474 (SEQ ID NO: 10) from the ATG of the open reading frame (position 317 for human IL-15 GenBank U14407 and position I for the purposes of the invention; see FIG. 8). Exemplary target sequences (RT) (SEQ ID NO:2, 4, 6, 8, and 10) and exemplary ribozymes (RZ) (SEQ ID NO: 1, 3, 5, 7, and 9) are shown in FIG. 9.

The present invention also includes a method for suppression of gene expression, which includes administering to a cell a suppressive-effective amount of the nucleic acid construct including a ribozyme of the invention or combinations thereof, so that the expression of IL-15 is suppressed.

The invention provides a method for producing a class of ribozymes which exhibit a high degree of specificity for the desired target RNA. The ribozyme is preferably targeted to a highly conserved sequence region of IL-15-encoding mRNA such that specific treatment of a disease or condition can be provided with either one or several enzymatic nucleic acids. Such ribozymes can be delivered exogenously to specific cells as required.

Ribozymes are added directly, or can be complexed with cationic lipids, packaged within liposomes, or otherwise delivered to target cells. The ribozyme or ribozyme complexes can be locally administered to relevant tissues ex vivo, or in vivo through injection, infusion pump or stent, with or without incorporation in biopolymers. Alternatively, the ribozymes can be expressed from DNA or RNA vectors that are delivered to the cells, so that the RNA molecules are expressed within cells from either inducible or constitutive eukaryotic promoters. These recombinant vectors containing the ribozyme are preferably DNA plasmids, adenovirus, retroviral or adeno-associated virus vectors. However, other mammalian cell vectors that direct the expression of RNA may be used for this purpose. The recombinant vectors capable of expressing the ribozymes can be locally delivered as described above. Once expressed the ribozymes cleave the target mRNA.

A wide range of promoters may be utilized to direct expression of ribozymes directed against IL-15 mRNA, including viral or mammalian promoters. Cell or tissue specific promoters can be utilized to target expression of gene sequences in specific cell populations. Suitable mammalian and viral promoters for use in the present invention are known. For example promoters such as the simian virus 40 (SV40), cytomegalovirus (CMV), β-actin, metallothionen, or imunoglobulin promoters can be used.

The choice of the particular heterologous promoter region as "regulatory nucleotide sequence" of the invention is dictated by the spatial and temporal pattern of expression that is desired for the ribozyme. Promoter regions include eukaryotically derived promoters which predominantly direct expression in, for example the immune system (e.g., circulating immunological cell or thymus or spleen) or the musculoskeletal system (e.g. muscle or joint tissue).

Alternatively, non-eukaryotically-derived promoters such as virally-derived and prokaryotically derived promoters can also be used in the present invention. Such virally-derived promoters include, but are not limited to MMTV and MoSV LTR, SV40 early region, RSV, or CMV LTR, which direct expression of viral or host genes in specific tissues and in many cell types.

Promoters useful in the invention include both constitutive and inducible natural promoters as well as engineered promoters. To be most useful, an inducible promoter should (1) provide low expression in the absence of the inducer; (2) provide high expression in the presence of inducer; (3) use an induction scheme that does not interfere with the normal physiology of the cell; (4) have no effect on the expression of other genes. Both constitutive and inducible promoters and enhancers are known in the art. The promoters used in the constructs of the present invention can be modified, if desired to affect their control characteristics.

The regulatory sequence can also include "enhancer" regions. Enhancer regions, as used herein, refer to DNA sequences that affect transcription of a gene by RNA polymerase II, without regard to position or orientation. An enhancer region can be thousands of base pairs from a transcription unit and still affect its transcription. Examples of known enhancers include the immunoglobulin heavy (mu) chain or light (kappa) chain enhancers and the SV40 72-base pair repeats.

The construct may optionally include a stabilizing region such as a "stem loop" structure. This is a structure, generally of 16 to 50 nucleotides in length, wherein the resulting RNA transcript of the construct is predicted to form a hairpin structure. This region, when present, is able to reduce the rate of intracellular degradation of the resulting RNA transcript as compared with an identical RNA transcript that does not contain the stabilizing region (e.g., U.S. Pat. No. 5,624,803, herein incorporated by reference).

The construct may also optionally include a 5' cap structure, which prevents degradation of the product at the 5' end. The stability of the resulting RNA transcripts is strongly enhanced by the capping. The optional "capping segment", such as a trimethylguanosine cap or a γ-monomethyl phosphate cap, is useful in combination with a stem loop structure (U.S. Pat. No. 5,624,803).

Phosphodiester-linked polynucleotides are particularly susceptible to the action of nucleases in serum or inside cells, and therefore in a preferred embodiment the enzymatic mRNA of the present invention are phosphorothioate or methyl phosphonate-linked analogues, which have been shown to be nuclease-resistant. Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with CH2 NH O CH2, CH2 N(CH3) O CH2, CH2 O N(CH3) CH2, CH2 N(CH3) N(CH3) CH2 and O N(CH3) CH2 CH2 backbones (where phosphodiester is O P O CH2). Also preferred are oligonucleotides having morpholino backbone structures (Summerton, J. E. and Weller, D. D., U.S. Pat. No. 5,034,506). In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone (P. E. Nielsen, M. Egholm, R. H. Berg, O. Buchardt, Science, 1991, 254, 1497). Other preferred oligonucleotides may contain alkyl and halogen-substituted sugar moieties comprising one of the following at the 2' position: OH, SH, SCH3, F, OCN, OCH3OCH3, OCH3O(CH2)nCH3, O(CH2) nNH2 or O(CH2)nCH3 where n is from 1 to about 10; C1 to C10 lower alkyl, substituted lower alkyl, alkaryl or aralkyl; Cl; Br; CN; CF3; OCF3; O, S, or N-alkyl; O, S or N alkenyl; SOCH3; SO2CH3; ONO2; NO2; N3; NH2; heterocycloalkyl; heterocycloalkaryl; aminoalkylamino; polyalkylamino; substituted silyl; an RNA cleaving group; a cholesteryl group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form or "universal base" such as inosine. The preparation of base-modified nucleosides, and the synthesis of modified oligonucleotides using said base-modified nucleosides as precursors, has been described, for example, in U.S. Pat. Nos. 4,948,882 and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (e.g., U.S. Pat. No. 5,118, 802) and can be used similarly. Persons of ordinary skill in this art will be able to select other linkages for use in the invention. These modifications also may be designed to improve the cellular uptake and stability of the polynucleotides. It is understood that depending on the route or form of administration of the ribozymes of the invention, the modification or site of modification will vary (e.g., 5' or 3' modification). One of skill in the art could readily determine the appropriate modification without undue experimentation.

Various viral vectors which can be utilized for the enzymatic RNA which specifically cleaves mRNA encoding IL-15, described herein, include adenovirus, adeno-associated virus, herpes virus, vaccinia, or, an RNA virus such as a retrovirus. Preferably, the retroviral vector is a derivative of a murine or avian retrovirus. Examples of retroviral vectors in which a single foreign gene can be inserted include, but are not limited to: Malawian murine leukemia virus (MoMuLV), Harvey murine sarcoma virus (HaMuSV), murine mammary tumor virus (MuMTV), and Rous Sarcoma Virus (RSV). Recently, it has been shown that murine leukemia virus-based retroviral vectors can be used to deliver exogenous genes to naive and chronically inflamed joints in vivo (Ghivizzani, S.C., et al., 1997, Gene Therapy 4: 977–982, herein incorporated by reference). When the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated.

The vector can be target specific by inserting a sequence of interest into the viral vector, along with another gene which encodes the ligand for a receptor on a specific target cell. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the enzymatic RNA of the invention.

It may be desirable to deliver the constructs of the invention directly to the cell without the requirement for expression, therefore, a promoter or other regulatory nucleic acid is optional. One example of a targeted delivery system for antisense polynucleotides is a colloidal dispersion system. Colloidal dispersion systems include macromolecule complexes, nanocapsules, microspheres, beads, or lipid-based systems including oil-in-water emulsions, micelles, mixed micelles, and liposomes or liposome formulations. The suitable colloidal system can use is liposomes, which are artificial membrane vesicles that are useful as delivery vehicles in vitro and in vivo. The liposme formulations may have net cationic, anionic, or neutral charge characteristics and are useful with in vitro, in vivo and ex vivo delivery methods. It has been shown that large unilamellar vesicles (LUV), which range in size from 0.2–4.0 $\mu$m can encapsulate a substantial percentage of an aqueous buffer containing large macromolecules.

RNA, DNA, and intact virions can be encapsulated within the aqueous interior and be delivered to cells in a biologically active form (Fraley, et al, 1981 *Trends Biochem. Sci.,* 6:77). In addition to mammalian cells, liposomes have been used for delivery of polynucleotides in plant, yeast, and bacterial cells. For a liposome to be an efficient gene transfer vehicle, it should have the following characteristics: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., 1988, *Biotechniques,* 6:682).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. The constructs of the invention can also be delivered as a naked gene expression vector. This means that the construct is not associated with a delivery vehicle (e.g., liposomes or colloidal particles). One of the principal advantages touted for naked vectors has been the lack of immune responses stimulated by the vector itself.

The constructs of the invention can be delivered alone or in conjunction with other agents such as immunosuppressive drugs or other ribozymes. For example, ribozymes that specifically cleave mRNA encoding another cytokine, such as TNF-A or interferon-y, can be used with the enzymatic RNA molecules of the invention. Further, combinations of the ribozymes of the invention, e.g., SEQ ID NO: 1, 3, 5, 7 or 9, can be used. Agents useful in treating rheumatoid arthritis, such as colloidal gold or methotrexate, may also be used in conjunction with ribozymes which specifically cleave IL-15. Anti-inflammatory agents, such as non-steroidal anti-inflammatory drugs, corticosteroids, and hydroxychloroquine, immunosuppressive agents such as cyclosporine, and cytotoxic drugs such as cyclophosphamide, azathioprine, may also be used in conjunction with the enzymatic RNA molecules of the invention.

The invention includes a method of treatment comprising administering to a mammalian (human) cell in vitro or in vivo a pharmaceutical formulation comprising a pharmaceutically acceptable excipient carrier having dispersed therein a therapeutically effective amount of an enzymatic RNA which specifically cleaves IL-15 mRNA or combination of ribozymes.

The invention also includes a composition for therapy comprising an effective amount of an enzymatic RNA of the invention or combination thereof, and a physiologically acceptable excipient or carrier.

Physiologically acceptable and pharmaceutically acceptable excipients and carriers are well known to those of skill in the art. By "physiologically or pharmaceutically acceptable carrier" as used herein is meant any substantially non-toxic carrier for administration in which an enzymatic mRNA of the invention will remain stable and bioavailable when used. For example, the enzymatic RNA of the invention can be dissolved in a liquid, dispersed or emulsified in a medium in a conventional manner to form a liquid preparation or is mixed with a semi-solid (gel) or solid carrier to form a paste, ointment, cream, lotion or the like.

Suitable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, or gum arabic, synthetic polymers, such as discussed below, alcohols, polyols, water and the like. Preferably, because of its non-toxic properties, the carrier is a water miscible carrier composition that is substantially miscible in water. Such water miscible carrier composition can include those made with one or more ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions or gels.

The carrier can comprise a sustained release or delayed release carrier. The carrier is any material capable of sustained or delayed release of the enzymatic RNA specifically directed against IL-15 mRNA to provide a more efficient administration resulting in one or more of less frequent and/or decreased dosage of the protein growth factor, ease of handling, and extended or delayed effects. The carrier is capable of releasing the oligomer when exposed to the environment of the area for diagnosis or treatment or by diffusing or by release dependent on the degree of loading of the oligomer to the carrier in order to obtain releases of the enzymatic RNA of the invention. Non-limiting examples of such carriers include liposomes, microsponges, microspheres, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like.

Preferably, the sustained or delayed release carrier is a liposome, microsponge, microphere or gel.

The compositions of the invention are administered by any suitable means, including injection, transdermal, intraocular, transmucosal, bucal, intrapulmonary, and oral.

Preferably the carrier is a pH balanced buffered aqueous solution for injection. However, the preferred carrier will vary with the mode of administration.

The compositions for administration usually contain from about 0.0001% to about 90% by weight of the enzymatic RNA of the invention compared to the total weight of the composition, preferably from about 0.5% to about 20% by weight of the enzymatic mRNA of the invention compared to the total composition, and especially from about 2% to about 20% by weight of the enzymatic mRNA of the invention compared to the total composition.

The effective amount of the enzymatic mRNA of the invention used for therapy or diagnosis of course can vary depending on one or more of factors such as the age and weight of the patient, the type of formulation and carrier ingredients, frequency of use, the type of therapy or diagnosis preformed and the like. It is a simple matter for those of skill in the art to determine the precise amounts to use taking into consideration these factors and the present specification.

Transgenic Animals

In a further embodiment, a transgenic animal can be developed using the novel construct and method of the invention in order to identify the impact of increased or decreased IL-15 levels on a particular pathway or phenotype. Protocols useful in producing such transgenic animals are described below. The protocol generally follows conventional techniques for introduction of expressible transgenes into mammals. Those of ordinary skill in the art will be familiar with these applications and will be able to apply the techniques in the context of the present invention without undue experimentation.

For example, embryonic target cells at various developmental stages can be used to introduce transgenes encoding an IL-15 ribozyme. Different methods are used depending on the stage of development of the embryonic target cell. The zygote is the best target for microinjection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster, et al., 1985, *Proc. Natl. Acad Sci. USA* 82:4438–4442). As a consequence, all cells of the transgenic non-human animal will carry the incorporated transgene. In general, this will also be reflected in the efficient transmission of the transgene to offspring of the founder since 50% of the germ cells will harbor the transgene. Microinjection of zygotes is a suitable method for incorporating transgenes in practicing the invention.

Retroviral infection can also be used to introduce a transgene encoding an ribozyme which specifically cleaves IL-15 mRNA into a non-human animal. The developing non-human embryo can be cultured in vitro to the blastocyst stage. During this time, the blastomeres can be targets for retroviral infection (Jaenisch, 1976, *Proc. Natl. Acad. Sci. USA* 73:1260–1264). Efficient infection of the blastomeres is obtained by enzymatic treatment to remove the zona pellucida (Hogan, et al., 1986, *Manipulating the Mouse Embryo*, Cold Spring Harbor Laboratory Press, Cold Spring Harbor, N.Y.). The viral vector system used to introduce the transgene encoding a ribozyme which specifically cleaves IL-15 mRNA is typically a replication-defective retrovirus carrying the transgene (Jahner, et al., 1985, *Proc. Natl. Acad. Sci. USA* 82:6927–6931; Van der Putten, et al., *Proc Natl. Acad. Sci. USA* 82:6148–6152). Transfection is easily and efficiently obtained by culturing the blastomeres on a monolayer of virus-producing cells (Van der Putten, supra; Steward, et al., 1987, *EMBO J.*, 6:383–388).

Alternatively, infection can be performed at a later stage. Virus or virus-producing cells can be injected into the blastocoele (Jahner, et al., 1982, *Nature*, 298:623–628). Most of the founder animals will be mosaic for the transgene since incorporation occurs only in a subset of the cells which formed the transgenic non-human animal. Further, the founder animals may contain various retroviral insertions of the transgene at different positions in the genome which generally will segregate in the offspring. In addition, it is also possible to introduce transgenes encoding an IL-15 ribozyme into the germ line, albeit with low efficiency, by intrauterine retroviral infection of the midgestation embryo (Jahner, et al., supra, 1982).

A third type of target cell for introduction of heterologous nucleic acid sequences is the embryonal stem cell (ES). ES cells are obtained from pre-implantation embryos cultured in vitro and fused with embryos (Evans, et al., 1981, *Nature*, 292:154–156; Bradley, et al., 1984, *Nature*, 309:255–258,; Gossler, et al, 1986, *Proc. Natl. Acad. Sci. USA*, 83:9065–9069; and Robertson, et al., 1986, *Nature*, 322:445–448). Transgenes encoding ribozymes which specifically cleave IL-15 mRNA can be efficiently introduced into the ES cells by DNA transfection or by retro-virus-mediated transduction. These transformed ES cells can thereafter be combined with blastocysts from a non-human animal. The ES cells will thereafter colonize the embryo and contribute to the germ line of the resulting chimeric animal (see for review, Jaenisch, 1988, *Science*, 240:1468–1474). Any ES cell may be used is accordance with the present invention. It is, however, preferred to use primary isolates of ES cells. Such isolates may be obtained directly from embryos such as with the CCE cell line disclosed by Robertson, E. J., in Current Communications in Molecular Biology, Capecchi, M. R. (Ed.) Cold Springs Harbor Press, Cold Springs Harbor, N.Y. (1989), pp.39–44), or from the clonal isolation of ES cells from the CCE cell line (Scwartzberg, P. A. et al., 1989, *Science* 246:799. ES cells may be derived or isolated from any species, although cells derived or isolated from mammals such as rodents, rabbits, and non-human primates are preferred.

The cre/lox system as described in U.S. Pat. No. 4,959,317, incorporated herein by reference, can be utilized in the production of transgenic animals. A first and second loxP DNA sequence is introduced into cells connected by a preselected antisense or replacement gene, such as a ribozyme which specifically cleaves IL-15 mRNA, herein referred to as a "target transgene".

The "target transgene" of interest can be a complete gene or any other sequence of nucleotides including those of homologous, heterologous, or synthetic origin. The target transgene sequence can be for example, an antisense or replacement gene for a structural protein, and enzyme, a regulatory molecule, or a cytokine such as IL-15. The target transgene may also be a gene of undetermined function. Using tissue-specific or developmentally-specific regulatory sequences (as described above) to direct expression of the 
target transgene, a function could be identified. If the first and second lox sites have the same orientation (direct repeats), activation of the regulatory nucleotide sequence of the transactivator transgene results in a deletion of the target transgene DNA, such that ablation or modification of activity results. If the first and second lox sites have opposite orientation (inverted repeats), activation of the regulatory nucleotide produces an inversion of the nucleotide sequence of the target transgene.

The construct of the invention may be used to introduce DNA sequences into the germ line cells of "non-humans" to create transgenic animals. Mice are useful as transgenic animals. However, other non-humans of the invention include but are not limited to other rodents (e.g., rat, hamster), rabbits, chickens, sheep, goats, pigs, cattle, and non-human primates.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Gene Therapy

The present invention provides gene therapy for the treatment of a disease which is associated with IL-15. such therapy would achieve its therapeutic effect by introduction of the appropriate ribozyme which specifically cleaves IL-15 mRNA into cells of subjects having the disorder. Delivery of the IL-15 ribozyme can be achieved using a recombinant expression vector such as a chimeric virus or a colloidal dispersion system.

Gene therapy methods as described herein can be performed in vivo or ex vivo. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a sequence encoding an ribozyme which specifically cleaves IL-15 mRNA into the viral vector, along with another gene which encodes the ligand for a receptor on a specific target cell, for example, the vector is now target specific. Preferred targeting is accomplished by using an antibody to target the retroviral vector. Those of skill in the art will know of, or can readily ascertain without undue experimentation, specific polynucleotide sequences which can be inserted into the retroviral genome, for example, to allow target specific delivery of the retroviral vector containing the ribozyme.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to 2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for ribozymes that specifically cleave IL-15 mRNA is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

Other means of encapsulating and delivering ribozymes targeted against IL-15 mRNA or transfected cells containing ribozymes that specifically cleave IL-15 mRNA in operable linkage with regulatory elements for expression, will be known to those of skill in the art.

EXAMPLES

The invention is farther described in the following examples, which are not intended to limit the scope of the invention described in the claims.

Example 1

Ribozyme Design

Based on the gene sequence of the human IL-15 gene, two IL-15 specific 42-nucleotide hammerhead ribozyme constructs were designed. The first was designed to cleave at the GUC sequence located at nucleotide 97 (FIG. 1), and the second was designed to cleave at the GUC sequence located at position 126 (FIG. 2) of IL-15 mRNA. The catalytic portion of the ribozyme, the catalytic center of each of the ribozymes contains ribonucleotides, whereas the three stems contain deoxyribonucleotides. The DNA/RNA composition of these ribozyme constructs offers improved stability in vivo and enhanced cellular activity (Taylor et al., 1992, *Nucleic Acids Research* 20: 4559–65, herein incorporated by reference). The ribozymes were synthesized on a commercial DNA synthesizer, using techniques well known in the art.

Example 2

Cleavage of IL-15 synthetic RNA in vitro

A synthetic RNA fragment of IL-15 RNA (21 nucleotides in length) served as an in vitro substrate for the ribozymes described in Example 1. The synthetic IL-15 RNA was 5'-end labeled as follows:

A 50 μl reaction volume containing either DNA or RNA was incubated at 37° C. for 90 minutes in 50 mM Tris-HCL, pH 7.6, 6 mM $MgCl_2$, 100 mM DTT, 50 μCi of γ-$^{32}$P ATP (7000 Ci/mmol). The reaction was initiated by adding T4 polynucleotide kinase (10–15 units). The unincorporated γ-$^{32}$P ATP was removed by separation on a Sephadex G-25 column and the resulting labeled oligomer was precipitated with ethanol. After centrifugation the resulting pellet was dissolved in gel loading buffer and further purified by polyacrylamide gel electrophoresis.

The labeled DNA/RNA was isolated from the gel by a crush and soak method using 0.6 M ammonium acetate, 1 mM EDTA, and 0.1% SDS.

Upon cleavage with the ribozymes described above, the 5' end labeled RNA should yield an approximately 12 nucleotide cleavage product. For in vitro cleavage reactions, a 10 μl reaction volume containing approximately 50–100 ng of ribozyme and 50,000 cpm of target RNA in 50 mM Tris-HCl, pH=8.0 was mixed with 20 mM $MgCl_2$ to start the reaction and then incubated for 60 minutes. The reaction was stopped by the addition of a gel loading buffer and the samples were heated at 90° C. for one minute, chilled on ice, and gel electrophoresed. Samples were electrophoresed on 8% polyacrylamide, 0.25% bis-acrylamide gels buffered with 89 mM Tris, 89 mM boric acid (pH=7.5), and 20 mM $MgCl_2$ for 4.5 hours at 10 V/cm at 6° C. Gels were then dried and autoradiographed.

Figure 1:
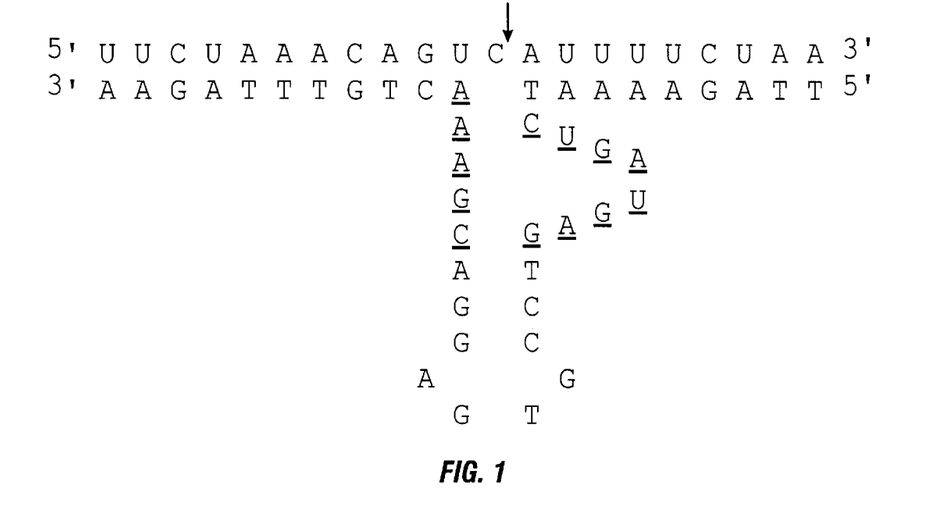
FIG. 1 is a diagram illustrating the sequence of an IL-15 mRNA targeted DNA-RNA hammerhead ribozyme (SEQ ID NO.: 1) and the complementary mRNA encoding IL-15. The ribozyme (bottom) cleaves the GUC sequence at position 97 of IL-15 mRNA (top) as indicated by the arrows. The sequence of the target binding portion (SEQ ID NO:2) of the ribozyme is underlined.
Figure 2:
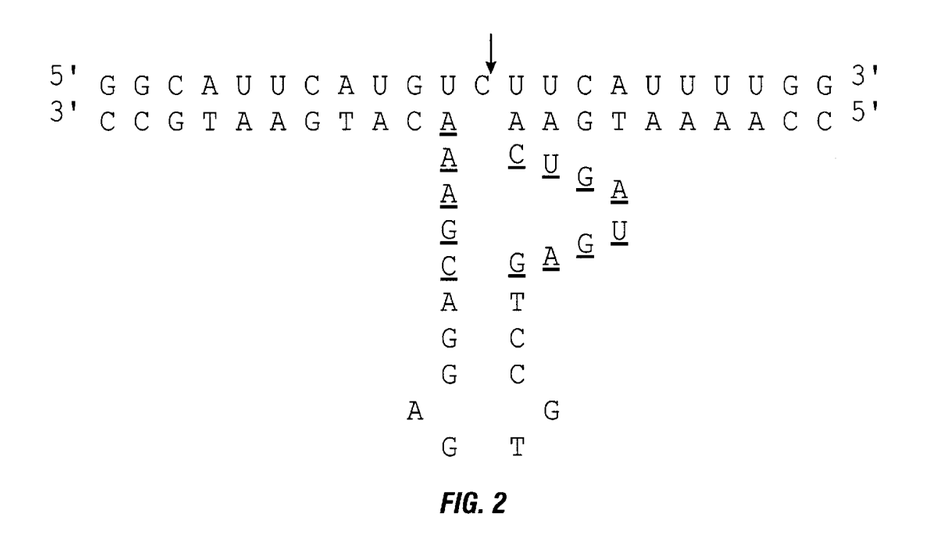
FIG. 2 is a diagram illustrating the sequence of an IL-15 mRNA targeted DNA-RNA hammerhead ribozyme (SEQ ID NO.:3) and the complementary mRNA. The ribozyme (bottom) cleaves the GUC sequence at position 126 of IL-15 mRNA (top) as indicated by the arrows. The sequence of the target binding portion (SEQ ID NO:4) of the ribozyme is underlined.
Figure 3:
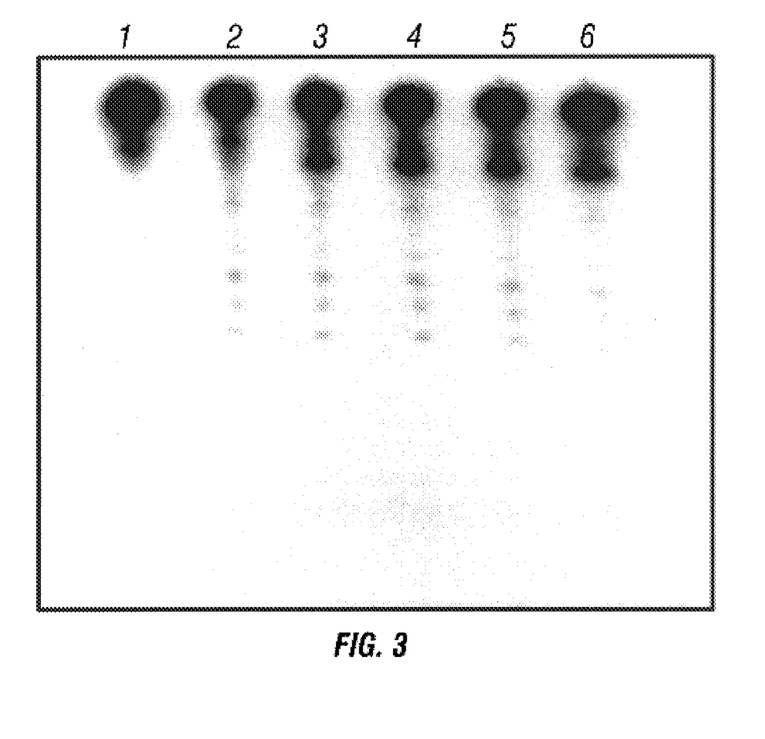
FIG. 3 is an autoradiograph showing the cleavage of IL-15 RNA 22-mer substrate by the ribozyme which cleaves GUC at position 97 in vitro. Lane 1 illustrates the lack of target cleavage in the absence of ribozyme, lanes 2 illustrates the formation of cleavage product in the presence of 500 ng of ribozyme in the absence of magnesium, and lanes 3–6 illustrates the formation of cleavage product in the presence of magnesium and reduced amounts of ribozyme.
Figure 4:
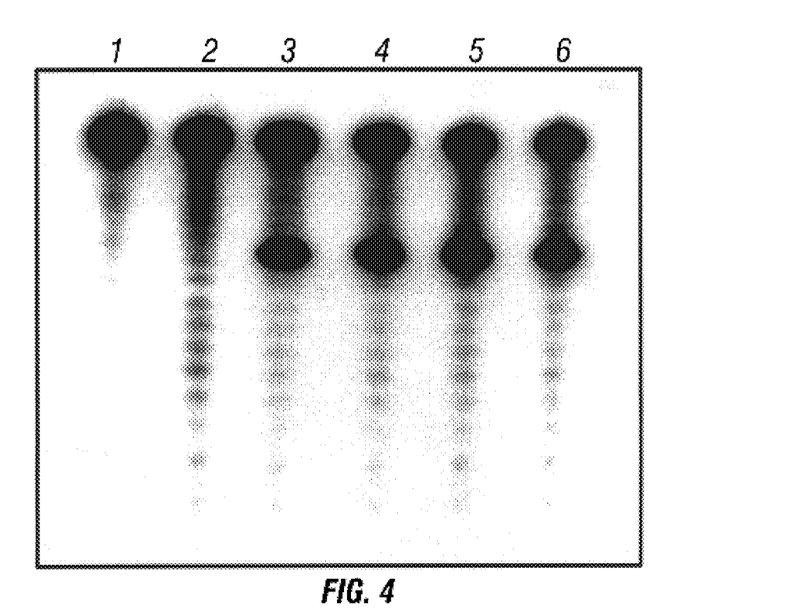
FIG. 4 is an autoradiograph illustrating the cleavage of IL-15 RNA 22-mer substrate by the ribozyme which cleaves GUC at position 126 in vitro. Lane 1 illustrates the lack of target cleavage in the absence of ribozyme, lanes 2 illustrates the formation of cleavage product in the presence of 500 ng of ribozyme in the absence of magnesium, and lanes 3–6 illustrates the formation of cleavage product in the presence of magnesium and reduced amounts of ribozyme.

Upon incubation of the synthetic IL-15 fragment with either ribozyme construct, an approximately 12 nucleotide cleavage fragment was detected. The amount of cleavage product increased with increasing amounts of ribozyme. No cleavage occurred in the absence of either magnesium or ribozyme (see FIGS. 3 and 4).

Example 3

Optimization

To evaluate the conditions at which the ribozyme optimally cleaved the RNA substrate, the cleavage reactions (as described above in Example 2) were performed under a variety of conditions. To assess the optimum temperature of the reaction, cleavage was performed at temperatures from 25° C. to 65° C. The optimum temperature for RNA cleavage was found to be 37° C. (physiological temperature). An equivalent amount of cleavage product was generated at 42° C., while at 55° C. the amount of cleavage product was greatly diminished, and at 65° C. no cleavage product could be detected (see FIG. 5).

Figure 5:
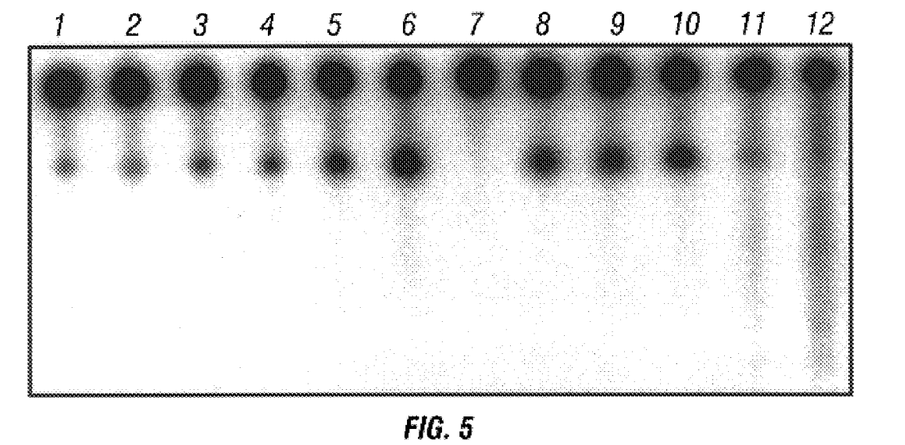
FIG. 5 is an autoradiograph showing the optimization of conditions for the cleavage of IL-15 at position 126. Lanes I to 6 are incubated at 37 C for the indicated times. Lanes 8–12 show incubation for 2 hours at the temperature shown. Lane 7 is target alone.
Figure 6:
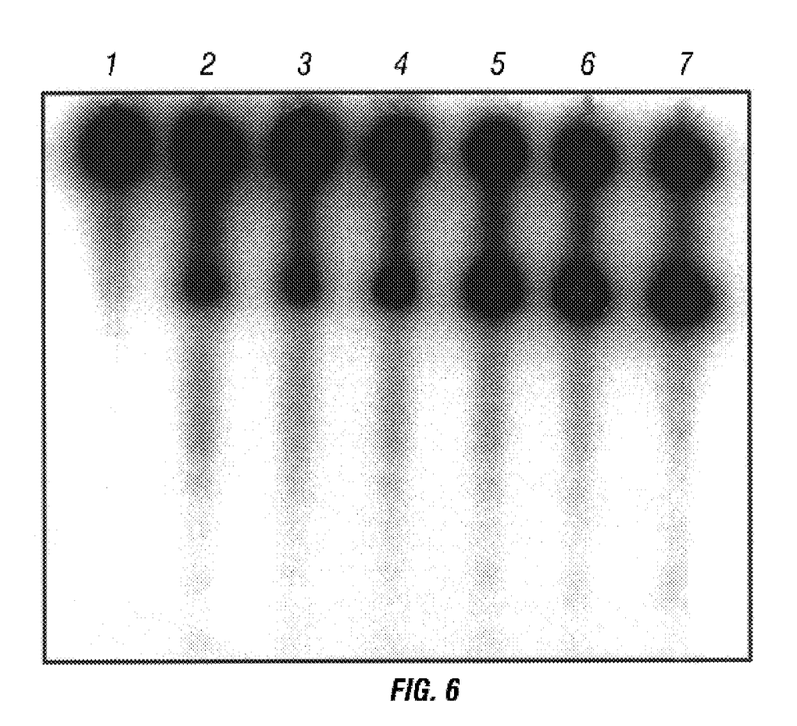
FIG. 6 is an autoradiograph showing the effect of concentration on the cleavage reaction. cleavage reactions were carried out at 37° C. for 2 hours in the presence of 50,000 CPM of substrate and increasing amounts of ribozyme. Lane I shows the reaction product without the addition of ribozyme, and lanes 2–7 show the reaction products obtained with 2, 5, 10, 20, 50, and 100 mM ribozyme, respectively.

To evaluate the time course of the reaction similar cleavage reactions were performed (as described in Example 2), and the production of the reaction product was evaluated. Product formation could be detected after reaction for only one minute at room temperature. As shown in FIG. 5, Product formation increased several fold after two hours of incubation. In order to consider the effects of pre-heating, a further series of reactions were performed. The results shown in FIG. 6 indicate that the amount of product obtained without pre-heating was equal to or greater than the amount of reaction product obtained with pre-heating.

Figure 7:
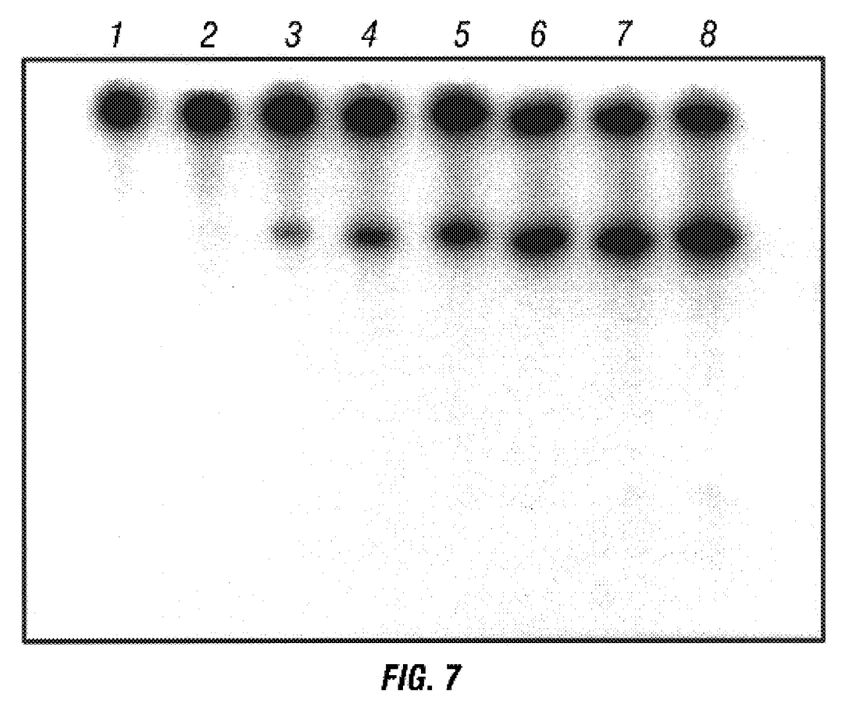
FIG. 7 is an autoradiograph illustrating the effect of magnesium concentration on the ribozyme-induced cleavage of IL-15 mRNA. Lane 1 shows the reaction product without the addition of ribozyme, lane 2–8 show the reaction products in the presence of ribozyme and with 0, 2, 5, 10, 20, 50, and 100 mM magnesium added, respectively.

The cleavage reaction also had an absolute requirement for divalent cations. To evaluate the dependence of the cleavage reaction on the divalent cations, the cleavage reaction (as described in Example 2) was performed with varying concentrations of $MgCl_2$. No cleavage product was produced in the absence of $MgCl_2$. The reaction rate was found to increase steadily with increasing $MgCl_2$ until a maximum was reached at 20 mM $MgCl_2$ (see FIG. 7).

Example 4

Inhibition of Il-15 expression in T cells

Peripheral blood and synovial fluid samples are collected from rheumatoid arthritis patients who satisfy the American College of Rheumatology 1987 criteria. The presence of IL-15 is assayed by ELISA using paired murine monoclonal antibodies as described (McInnes et al., 1997, op. cit.) Mononuclear cell fractions are obtained by density gradient centrifugation, and macrophages are enriched. Cells isolated from the synovium or peripheral blood and are maintained in RPMI supplemented with 10% fetal calf serum. The cells are then transfected with either a reporter gene expression vector or with the IL-15 ribozyme construct using a DOTAP liposome formulation (Boehringer Mannheim, 1 mg/ml) according to the manufacture's instructions. The presence of IL-15 is then again assayed using the ELISA described above. RNA is isolated using a technique such as magnetic porous glass direct mRNA purification technique (according to the manufacturer's instructions, CPC, Inc.), and Northern blot analyses are performed. Electrophoresis of 3.5 μg of mRNA is performed under denaturing conditions (Lehrach et al., 1977 *Biochemistry* 16:4743). The gel is exposed to 60 mjoules of UV light to facilitate transfer of RNA species, and the RNA is transferred to nylon membrane using the turboblotting system according to the manufacturer's instructions (Schleicher & Schuell). The membrane is washed briefly in 2×SSC, crosslinked with 125 mjoules of UV light and prehybridized in Expresshyb (Clontech) for half an hour at 68° C. Human cDNA probes encoding IL-15 are labeled by random priming (Feinberg et al.,1983, *Anal Biochem.* 132:6). The membrane is hybridized for 1 hour at 68° C., and is washed in 2×SSC/0.05% SDS at room temperature, followed by 0.1×SSC/0. 1% SDS at 50° C., and is exposed to X-ray film. Transcripts for IL-15 are substantially reduced or absent in those cells transfected with the IL-15 ribozyme.

Example 5

Transgenic Mice Expressing Ribozymes Directed Against IL-15

Transgenic mice that can produce ribozymes that specifically cleave IL-15 are produced according to methods well known in the art. For example, young female mice are injected with hormones to induce superovulation, and are mated. The one-celled embryos are collected, and the pronuclei injected with a purified DNA solution containing the constructs which encode ribozymes that specifically cleave IL-15 mRNA. The injected eggs are cultured briefly, and re-implanted into pseudopregnant female mice. Genomic DNA is prepared from each progeny, and analyzed by PCR or Southern blot to determine the mouse's genotype. Mice who carry the transgene are subsequently mated in order to produce a line of mice.

Using these method mice are produced which contain transgenes encoding the ribozymes of the invention. In order to target the ribozymes to specific cell types, transgenic mice are produced which carry genes encoding the ribozymes that specifically cleave IL-15 mRNA under the control of specific promoters. Examples of such constructs are genes encoding SEQ ID NO: 1 or SEQ ID NO:2 under the control 
of the MRP promoter, which specifically targets the expression of IL-15 ribozymes to macrophages.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. An isolated enzymatic RNA molecule which specifically cleaves human mRNA encoding interleukin-15 (IL-15).

2. The enzymatic RNA molecule of claim 1, wherein said enzymatic RNA molecule is a hammerhead ribozyme.

3. The enzymatic RNA molecule of claim 1, wherein said enzymatic RNA molecule is selected from the group consisting of a hairpin, hepatitis delta virus, group I intron, VS RNA, tetrahymena, and a RNAse P RNA motif.

4. The enzymatic RNA molecule of claim 1, wherein said enzymatic RNA comprises at least 5 bases complementary to said interleukin 15 (IL-15) mRNA.

5. The enzymatic RNA of claim 4, wherein said enzymatic RNA comprises a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

6. The enzymatic RNA molecule of claim 1, wherein said enzymatic RNA molecule comprises phosphorothioate or methyl phosphonate-linked analogues.

7. The enzymatic RNA molecule of claim 5, wherein said RNA molecule further comprises a stem loop structure.

8. The enzymatic RNA molecule of claim 5, wherein said enzymatic RNA molecule further comprises a 5' end modification.

9. The enzymatic RNA molecule of claim 8, wherein said 5' end modification is a 5' trimethylguanosine cap.

10. An expression vector comprising a nucleic acid encoding the enzymatic RNA molecule of claim 1.

11. The expression vector of claim 10, further comprising a promoter operably associated with the enzymatic RNA.

12. The expression vector of claim 10, wherein the enzymatic RNA molecule comprises a nucleic acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, or any combination thereof.

13. A mammalian cell comprising an enzymatic RNA molecule of claim 1, wherein said cell is in vitro.

14. The cell of claim 14, wherein said cell is a human cell.

15. The cell of claim 15, wherein the enzymatic RNA molecule comprises a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, or any combination thereof.

16. A method for inhibiting IL-15 production in a cell in vitro, the method comprising: administering to the cell an amount of an enzymatic RNA molecule sufficient to cleave specifically mRNA encoding interleukin-15 (IL-15) thereby inhibiting IL-15 production.

17. The method of claim 16, further comprising administering an enzymatic RNA molecule which specifically cleaves TNF-α.

18. The method of claim 16, wherein the enzymatic RNA molecule comprises a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, or any combination thereof.

---

```
                    SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
          (A) LENGTH: 42 base pairs
          (B) TYPE: nucleic acid
          (C) STRANDEDNESS: single
          (D) TOPOLOGY: linear (ii) MOLECULE TYPE:  RNA (xi) SEQUENCE DESCRIPTION: SEQ ID NO:1:

TTAGAAAATC UGAUGAGTCC GTGAGGACGA AACTGTTTAG AA                          42

(2) INFORMATION FOR SEQ ID NO:2:

(i) SEQUENCE CHARACTERISTICS:
          (A) LENGTH: 21 base pairs
          (B) TYPE: nucleic acid
          (C) STRANDEDNESS: single
          (D) TOPOLOGY: linear
```

```
        (ii) MOLECULE TYPE:  RNA (xi) SEQUENCE DESCRIPTION: SEQ ID NO:2:

UUCUAAACAG UCAUUUCUA A                                              21

(2) INFORMATION FOR SEQ ID NO:3:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE:  RNA (xi) SEQUENCE DESCRIPTION: SEQ ID NO:3:

CAAAATGAAC UGAUGAGTCC GTGAGGACGA AACATGAATG CC                      42

(2) INFORMATION FOR SEQ ID NO:4:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE:  RNA (xi) SEQUENCE DESCRIPTION: SEQ ID NO:4:

GGCAUUCAUG UCUUCAUUUU G                                             21

(2) INFORMATION FOR SEQ ID NO:5:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE:  RNA (xi) SEQUENCE DESCRIPTION: SEQ ID NO:5:

GTATCTCCGC UGAUGAGTCC GTGAGGACGA AACTCATGTG AA                      42

(2) INFORMATION FOR SEQ ID NO:6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE:  RNA (xi) SEQUENCE DESCRIPTION: SEQ ID NO:6:

UUCACAUGAG UCCGGAGATA C                                             21

(2) INFORMATION FOR SEQ ID NO:7:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE:  RNA
```

-continued (xi) SEQUENCE DESCRIPTION: SEQ ID NO:7:

CCATTAGAAC UGAUGAGTCC GTGAGGACGA AACAAGATGT T                      41

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: RNA     (xi) SEQUENCE DESCRIPTION: SEQ ID NO:8:

AACAUCUUGU CUUCUAAUGG                                              20

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear     (ii) MOLECULE TYPE: RNA     (xi) SEQUENCE DESCRIPTION: SEQ ID NO:9:

GAACATTTGC UGAUGAGTCC GTGAGGACGA AACAATATGT AC                     42

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: RNA     (xi) SEQUENCE DESCRIPTION: SEQ ID NO:10:

GUACAUAUUG UCCAAAUGUU C                                            21

(2) INFORMATION FOR SEQ ID NO:11:

(i) SEQUENCE CHARACTERISTICS:
        (A) LENGTH: 1202 base pairs
        (B) TYPE: nucleic acid
        (C) STRANDEDNESS: double
        (D) TOPOLOGY: linear     (ii) MOLECULE TYPE: DNA     (xi) SEQUENCE DESCRIPTION: SEQ ID NO:11:

TGTCCGGCGC CCCCCGGGAG GGAACTGGGT GGCCGCACCC TCCCGGCTGC GGTGGCTGTC    60

GCCCCCCACC CTGCAGCCAG GACTCGATGG AGAATCCATT CCAATATATG GCCATGTGGC   120

TCTTTGGAGC AATGTTCCAT CATGTTCCAT GCTGCTGCTG ACGTCACATG GAGCACAGAA   180

ATCAATGTTA GCAGATAGCC AGCCCATACA AGATCGTATT GTATTGTAGG AGGCATCGTG   240

GATGGATGGC TGCTGGAAAC CCCTTGCCAT AGCCAGCTCT TCTTCAATAC TTAAGGATTT   300

ACCGTGGCTT TGAGTAATGA GAATTTCGAA ACCACATTTG AGAAGTATTT CCATCCAGTG   360

CTACTTGTGT TTACTTCTAA ACAGTCATTT TCTAACTGAA GCTGGCATTC ATGTCTTCAT   420

TTTGGGCTGT TTCAGTGCAG GCTTCCTAA AACAGAAGCC AACTGGGTGA ATGTAATAAG    480

TGATTTGAAA AAAATTGAAG ATCTTATTCA ATCTATGCAT ATTGATGCTA CTTTATATAC   540

-continued

```
GGAAAGTGAT GTTCACCCCA GTTGCAAAGT AACAGCAATG AAGTGCTTTC TCTTGGAGTT     600

ACAAGTTATT TCACTTGAGT CCGGAGATGC AAGTATTCAT GATACAGTAG AAAATCTGAT     660

CATCCTAGCA AACAACAGTT TGTCTTCTAA TGGGAATGTA ACAGAATCTG GATGCAAAGA     720

ATGTGAGGAA CTGGAGGAAA AAAATATTAA AGAATTTTTG CAGAGTTTTG TACATATTGT     780

CCAAATGTTC ATCAACACTT CTTGATTGCA ATTGATTCTT TTTAAAGTGT TTCTGTTATT     840

AACAAACATC ACTCTGCTGC TTAGACATAA CAAAACACTC GGCATTTAAA ATGTGCTGTC     900

AAAACAAGTT TTTCTGTCAA GAAGATGATC AGACCTTGGA TCAGATGAAC TCTTAGAAAT     960

GAAGGCAGAA AAATGTCATT GAGTAATATA GTGACTATGA ACTTCTCTCA GACTTACTTT    1020

ACTCATTTTT TTAATTTATT ATTGAAATTG TACATATTTG TGGAATAATG TAAAATGTTG    1080

AATAAAAATA TGTACAAGTG TTGTTTTTTA AGTTGCACTG ATATTTTACC TCTTATTGCA    1140

AAATAGCATT TGTTTAAGGG TGATAGTCAA ATTATGTATT GGTGGGGCTG GGTACCAATG    1200

CT                                                                  1202
```

19. A composition comprising:

a pharmaceutically acceptable carrier; and
an isolated enzymatic RNA molecule which specifically cleaves human mRNA encoding interleukin-15 (IL-15).

20. The composition of claim 19, wherein the enzymatic RNA molecule comprises a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, or any combination thereof.

* * * * *